United States Patent [19]
Abraham

[11] Patent Number: 6,071,275
[45] Date of Patent: *Jun. 6, 2000

[54] LASER MICROSCOPE ADAPTOR APPARATUS

[75] Inventor: Martin David Abraham, Hod Hasharon, Israel

[73] Assignee: Laser Industries, Ltd., Tel Aviv, Israel

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/421,436

[22] Filed: Apr. 12, 1995

Related U.S. Application Data

[63] Continuation-in-part of application No. 08/368,994, Jan. 5, 1995, Pat. No. 5,688,682.

[51] Int. Cl.[7] ........................................... A61N 5/06
[52] U.S. Cl. ........................... 606/18; 606/2; 606/13
[58] Field of Search ............................ 606/213–219

[56] References Cited

U.S. PATENT DOCUMENTS

| | | | |
|---|---|---|---|
| 3,783,874 | 1/1974 | Koester et al. | 606/4 |
| 4,293,944 | 10/1981 | Izumita et al. | |
| 4,396,285 | 8/1983 | Presta et al. | 606/18 |
| 4,719,912 | 1/1988 | Weinberg | 606/4 |
| 5,128,509 | 7/1992 | Black et al. | |
| 5,220,344 | 6/1993 | Ferschl | |
| 5,353,073 | 10/1994 | Kobayashi | |

FOREIGN PATENT DOCUMENTS

| | | |
|---|---|---|
| 0492778 | 7/1992 | European Pat. Off. |
| 8706714 | 11/1987 | WIPO |
| 9215034 | 9/1992 | WIPO |
| 9316631 | 9/1993 | WIPO |

OTHER PUBLICATIONS

Sharplan Lasers, Inc. 712 Acuspot Commercial Publications 4 pages.

*Primary Examiner*—David M. Shay
*Attorney, Agent, or Firm*—Theresa A. O'Rourke; Richard I. Samuel; Friedman Siegelbaum LLP

[57] ABSTRACT

An adaptor attachable to a laser apparatus and to a microscope for directing a laser beam from the laser apparatus onto an object in a working plane as viewed via the microscope. The adaptor includes an optical system located in the path of the laser beam for focusing the laser beam onto an object in the working plane. The optical system includes a number of mirrors. The adaptor also includes a manipulatable mirror located between the optical system and the working plane. The manipulatable mirror is selectively manipulatable to direct the laser beam to any desired location in the working plane. Further the adaptor includes a focusser coupled to the optical system that is capable of selectively focusing and defocussing the laser beam.

3 Claims, 4 Drawing Sheets

LASER MICROSCOPE ADAPTOR APPARATUS

CROSS REFERENCE TO RELATED APPLICATION

This application is a continuation-in-part of application U.S. Ser. No. 08/368,994, filed Jan. 5, 1995, now U.S. Pat. No. 5,688,682, issued Nov. 18, 1997, and entitled LASER MICROSCOPE ADAPTOR APPARATUS WITH AUTOFOCUS.

FIELD AND BACKGROUND OF THE INVENTION

The present invention relates to a laser microscope adaptor apparatus with focusing capability over a large continuous range. The invention is particularly useful in surgical laser microscope apparatus for delivering a laser beam to an object, such as a tissue to be cut, removed, or coagulated and is therefore described below with respect to such application.

Surgical lasers are often used in microsurgery, such as ENT, neurosurgery or gynecology, wherein a working laser beam (e.g., from a $CO_2$ laser), and a visible aiming beam (e.g., from a HeNe laser), are directed to the surgical site through a microscope adaptor, commonly termed a laser micromanipulator which includes a joystick by which the surgeon can direct the laser beam over selected locations in the field of view.

Surgical microscopes can be used at fixed working distances or a range of variable distances depending on the sophistication of the microscope. In general each clinical application has its own particular working distance. For example, for vocal cord treatments, a working distance of 400 mm is normally used; whereas for neurosurgery, a working distance of 300 mm is normally used. Working distances are set either discretely by changing the objective lens on the microscope or continuously in newer microscope models. To focus the laser beam at the focal plane of the microscope, laser focusing mirrors in the micromanipulator are moved in accordance with the working distance set on the microscope.

OBJECT AND BRIEF SUMMARY OF THE INVENTION

An object of the present invention is to provide an adaptor attachable to a laser and to a microscope which can either focus or defocus the laser beam.

According to the present invention, there is provided an adaptor attachable to laser apparatus and to a microscope for directing a laser beam from the laser apparatus onto an object in a working plane as viewed via the microscope, comprising: an optical system to be located in the path of the laser beam for focusing the laser beam onto the object in the working plane; and a manipulatable mirror between the optical system and the working plane, which mirror is manipulatable to direct the laser beam to any desired location in the working plane.

It will be appreciated that the optical system which focuses the laser beam onto the object in the working plane may focus the laser beam to a very small diameter, e.g., for cutting tissue, or to a larger diameter, e.g., for ablating or coagulating tissue. In the latter case, the laser beam is sometimes referred to as being somewhat "defocused" to enlarge its diameter, and thereby to distribute the energy over a larger surface area.

According to further features in the preferred embodiments of the invention described below, the laser apparatus outputs a working laser beam and a visible aiming laser beam. The manipulatable mirror is dichroic to transmit visible light including the visible laser aiming beam from the object to the microscope, and fully reflect the working laser beam.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
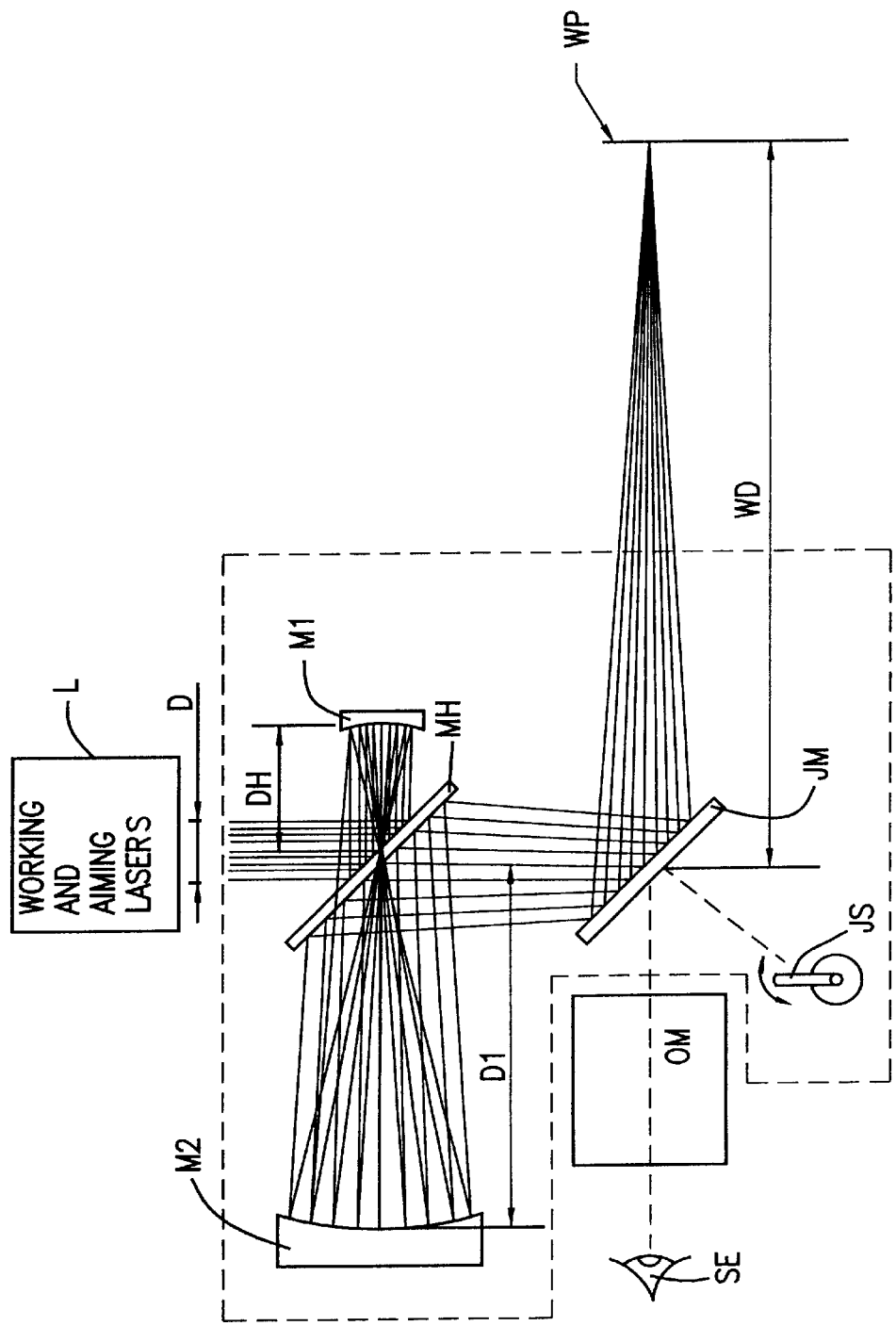
FIG. 1 illustrates a mirror based adaptor constructed in accordance with the present invention.

FIGS. 1–4 illustrate a mirror-based micromanipulator adaptor A in accordance with the present invention. As illustrated in FIG. 1 the input from the laser apparatus L, containing both the working laser beam (which is preferably from a $CO_2$ laser but is not meant to be limited as such) of diameter D and the visible aiming laser beam (which is preferably from a HeNe laser, but is not meant to be limited as such), of smaller diameter, are reflected off a 45° planar reflector MH. Reflector MH is silvered on both surfaces and has a small conical hole drilled in its center. The reflected input laser beams strike focusing mirror MH, which has a concave non-spherical surface and are reflected back towards the mirror M1. The input laser beams reflected from focusing mirror M1 come to a focus at a distance DH which is where the small conical hole in reflector MH is situated. The focused beams pass through the conical hole in reflector MH and strike a focusing mirror M2, which has a concave spherical surface, at a distance D1 from the small conical hole of planar reflector MH and are reflected back towards the reflector MH.

The working laser beam and visible aiming laser beam reflected off of mirror M2 converge to a focus or defocus, depending on the preference of the operator, in the working plane WP. The path to the focal plane includes the beams being reflected back to the planar reflector MH which reflects the beams to a dichroic mirror JM which reflects the beams onto the working plane WP.

The diameter of the conical hole must be large enough to pass all of the rays even if the laser delivery system is axially misaligned and small enough to prevent focused spot enlargement due to diffraction effects.

Joystick mirror JM is manipulatable by joystick JS to direct the beam to any desired location in the working plane WP. This mirror is dichroic and is located at an acute angle to the axis of the system such that it reflects the two laser beams to the working plane WP, but passes visible light therethrough to enable the viewer SE to view the working plane via the operating microscope OM. In the preferred embodiment of the invention the angle was 35° but it will be apparent to one skilled in the art that this angle may be acute angles other than 35°.

The optical system consists of mirrors with focal lengths that are independent of wavelength. In this way, the visible aiming laser beam lies in the same focal plane as the working laser beam and there is no transverse dispersion. This allows the surgeon to accurately focus or defocus the device with the aid of the aiming beam confident that both the minimum size of the working laser is achieved and that the center of the aiming beam lies accurately on the center of the working laser beam.

It will thus be seen that when the adaptor is installed on the operating microscope OM, the viewing optical axis is coincident with the laser beam axis, such that the surgeon's eye SE views the tissue as well as the laser aiming beam both of which pass through the dichroic mirror JM. The surgeon can thus precisely aim the working laser beam with respect to the tissue at the working plane through the operating microscope.

By rotating a ring on the adaptor the surgeon changes the distance D1 of the concave mirror M2 to the planar reflector MH. In this way he focuses the system at the required working distance.

Focusing is performed by observing the aiming beam through the microscope while rotating the working distance ring until the smallest aiming beam spot diameter is attained. Distance D1 can be adjusted to encompass the full range of working distances WD in all commercial operating microscopes. Since mirrors have exactly the same focal length irrespective of wavelength, the minimum $CO_2$ focused spot diameter will now be formed on the working plane WP.

Figure 2:
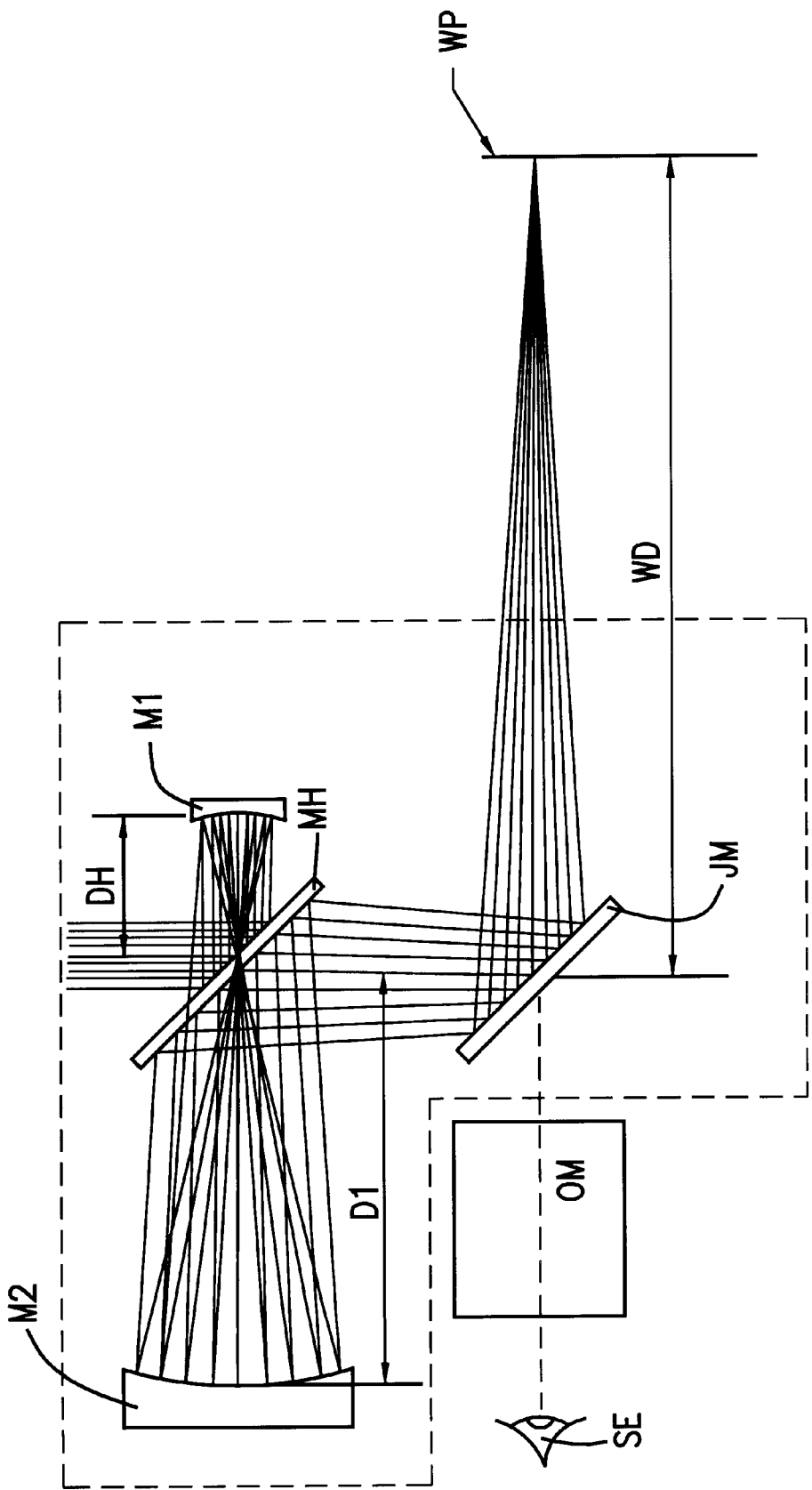
FIG. 2 illustrates how the laser beams in the adaptor of FIG. 1 are focused onto the object in the working plane when the working distance of the microscope is increased.

Referring to FIG. 2 and comparing it with FIG. 1 an example is given where the working distance has been increased. To focus the system and maintain the minimum spot diameter on the working plane WP the distance D1 is reduced. This, as explained, is achieved by rotating the working distance ring.

Figure 3:
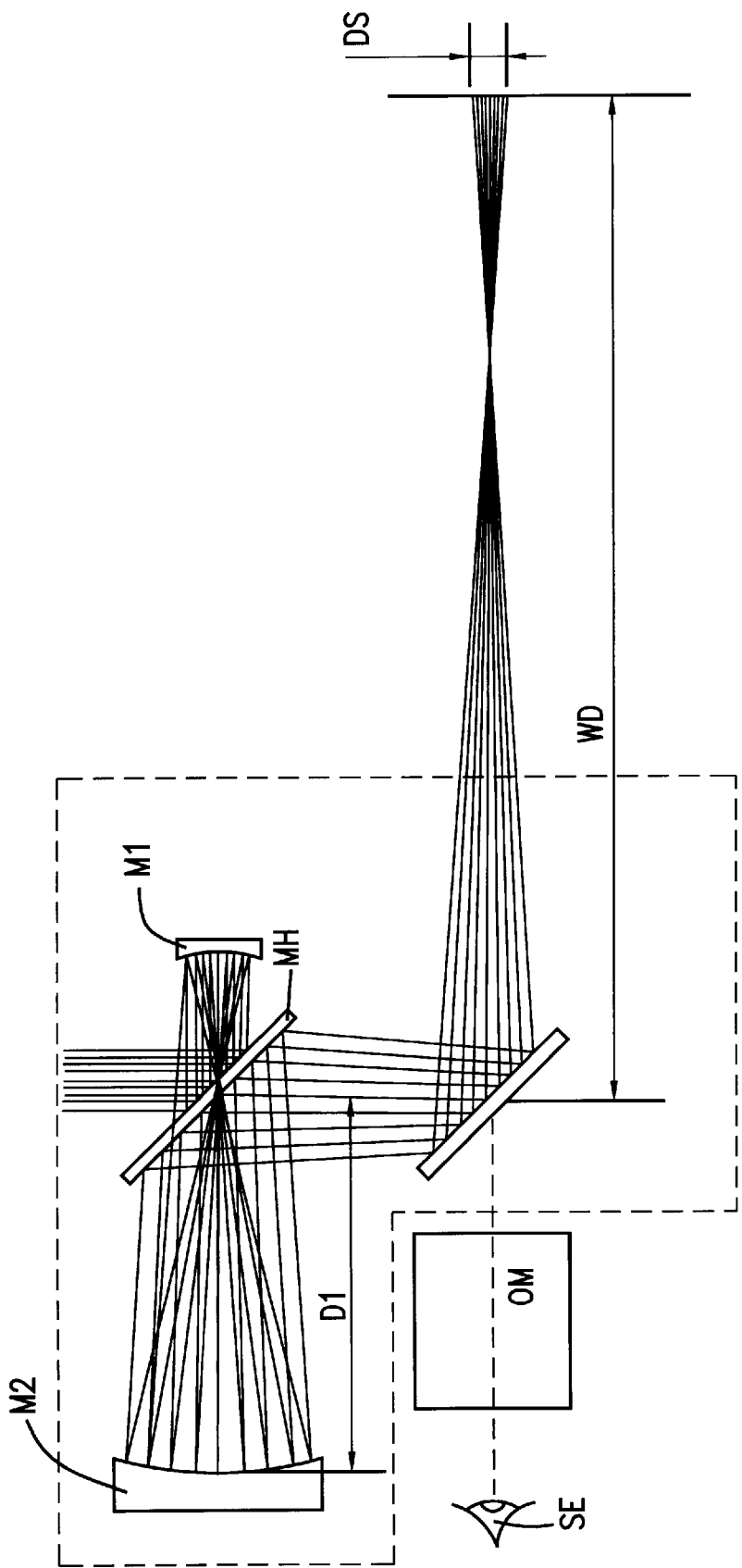
FIG. 3 illustrates the apparatus of FIG. 1 wherein the optical system is adjusted to enlarge the diameter or to "defocus", the laser beam.

Should the surgeon desire to work with an enlarged-diameter laser beam, e.g., for coagulation or ablation purposes, the surgeon can enlarge the diameter, or "defocus" the laser beam. FIG. 3 graphically displays this defocus mode at the given working distance WD. Here the surgeon would be operating with an enlarged "defocused" spot diameter as shown at DS, where the working plane WP is the focal plane of the operating microscope.

Figure 4:
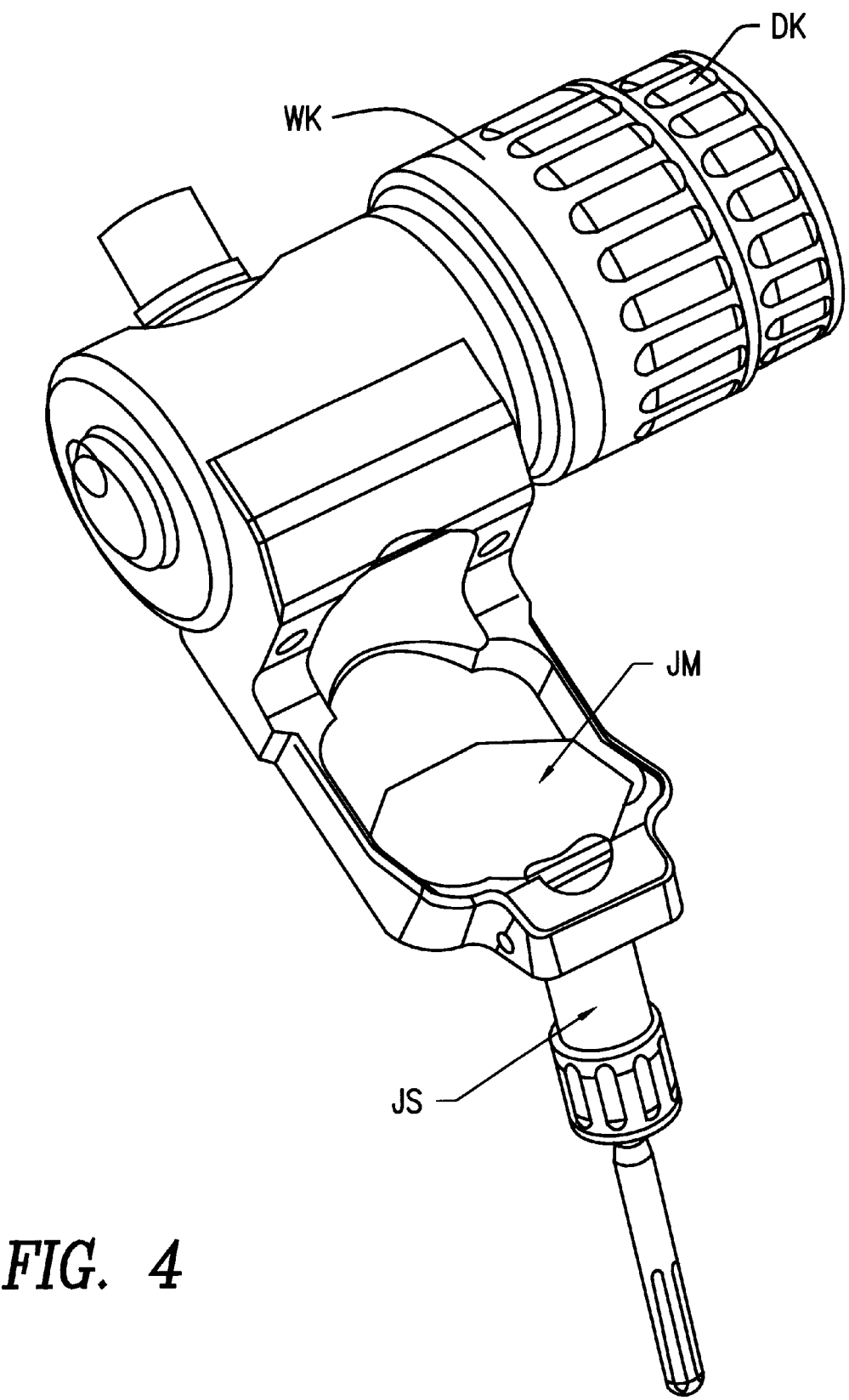
FIG. 4 is a perspective view of the apparatus of FIG. 1 showing details of a first ring for changing the working distance, a second ring for adjusting the focus and defocus settings, a joystick and a joystick mirror.

To achieve this defocus the distance D1 is increased beyond its focus position. In this way the system prefocuses in a method well known in the art. In order to overcome confusion between regulating the distance D1 for the purpose of working distance change and for focus-defocus operation two rings are incorporated. The first ring (working distance ring) is used to focus the system at the required working distance WD as already explained. The second defocus ring is used to increase the distance D1 beyond its focus position to a maximum fixed amount to effect defocus operation. The mechanical mechanism is designed such that rotating the working distance ring can only be achieved if the defocus ring is in the "focus" position. In this way dangerous post-focusing at a working distance beyond the working plane is avoided. FIG. 4 shows a mechanical drawing of the device with the working distance ring WK and the defocus ring DK clearly shown. The joystick mirror JM and joystick JS are also indicated.

While the invention has been described with respect to this embodiment, it will be appreciated that it is set forth merely for purposes of example, and that many other variations, modifications and applications of the invention may be made.

What is claimed is:

1. An adaptor for attachment to a laser apparatus and to a microscope for directing at least one laser beam from the laser apparatus onto an object in a working plane as viewed through the microscope, the adaptor comprising:

an optical system in alignment with the laser apparatus, said optical system comprising:
a reflector system for expanding said at least one laser beam from the laser apparatus, said reflector system including;
a planar reflector including oppositely disposed first and second reflecting surfaces and also including a substantially centrally positioned opening extending through said planar reflector; and
a first concave mirror disposed laterally with respect to said first reflecting surface of said planar reflector to receive said at least one laser beam reflected from said first surface and to focus said at least one laser beam at a focal plane at said opening;
a focusing mirror aligned with said reflector system, said focusing mirror including a second concave mirror disposed laterally with respect to said second reflecting surface of said planar reflector for focusing said at least one laser beam passing through said opening;
a manipulable mirror located between the optical system and the working plane, wherein the manipulable mirror is selectively manipulable to direct said at least one laser beam to any desired location in the working plane;
a focusser coupled to said optical system, said focusser being capable of selectively focusing and defocusing said at least one laser beam, said focusser comprising,
a working distance adjustment ring and a defocus ring both coupled to the second concave mirror; and
means responsive to the movement of said focusser for causing said second concave mirror to move relative to said planar reflector.

2. The adaptor of claim 1, wherein said manipulable mirror is dichroic.

3. An adaptor for attachment to a laser apparatus and to a microscope for directing at least one laser beam from the laser apparatus onto an object in a working plane as viewed through the microscope, the adaptor comprising:

an optical system in alignment with the laser apparatus, said optical system comprising:
a reflector system for expanding said at least one laser beam from the laser apparatus, said reflector system including;
a planar reflector including oppositely disposed first and second reflecting surfaces and also including a substantially centrally positioned opening extending through said planar reflector; and
a first concave mirror disposed laterally with respect to said first reflecting surface of said planar reflector to receive said at least one laser beam reflected from said first surface and to focus said at least one laser beam at a focal plane at said opening;

a focusing mirror aligned with said reflector system, said focusing mirror including a second concave mirror disposed laterally with respect to said second reflecting surface of said planar reflector for focusing said at least one laser beam passing through said opening;

a manipulable mirror located between the optical system and the working plane, wherein the manipulable mirror is selectively manipulable to direct said at least one laser beam to any desired location in the working plane and is dichroic;

a focusser coupled to said optical system, said focusser being capable of selectively focusing and defocusing said at least one laser beam, said focusser consisting,
a working distance adjustment ring and a defocus ring both coupled to the second concave mirror; and means responsive to the movement of said focusser for causing said second concave mirror to move relative to said planar reflector.

* * * * *